United States Patent [19]

Reinert et al.

[11] Patent Number: 4,895,981
[45] Date of Patent: Jan. 23, 1990

[54] PROCESS FOR IMPROVING THE PHOTOCHEMICAL STABILITY OF DYEINGS ON POLYESTER FIBRE MATERIALS

[75] Inventors: Gerhard Reinert, Allschwil; Kurt Burdeska, Basel, both of Switzerland

[73] Assignee: Ciba-Geigy Corporation, Ardsley, N.Y.

[21] Appl. No.: 331,071

[22] Filed: Mar. 24, 1989

Related U.S. Application Data

[63] Continuation of Ser. No. 156,771, Feb. 17, 1988.

[30] Foreign Application Priority Data

Feb. 27, 1987 [CH] Switzerland .............................. 751/87
Oct. 1, 1987 [CH] Switzerland ........................... 3820/87

[51] Int. Cl.⁴ ..................... C09B 67/10; C07D 239/70
[52] U.S. Cl. ............................................. 8/565; 8/567; 8/609; 544/249; 544/329; 544/334; 544/335; 544/331; 252/589
[58] Field of Search ......................... 8/565, 567, 609; 544/249, 329, 334, 335, 331; 252/589

[56] References Cited

U.S. PATENT DOCUMENTS 3,442,898  5/1969  Luethi .................................. 544/335
3,660,404  5/1972  Otterstedt et al. ........... 260/256.4 R

FOREIGN PATENT DOCUMENTS 1029045  5/1966  United Kingdom .

OTHER PUBLICATIONS

Chemical Abstracts, 81, 14635v, (1974).

Primary Examiner—Prince E. Willis
Assistant Examiner—Helene Klemanski
Attorney, Agent, or Firm—Edward McC. Roberts

[57] ABSTRACT

A process is described for improving the photochemical stability of dyeings on polyester fibre materials by means of UV absorbers of the formula

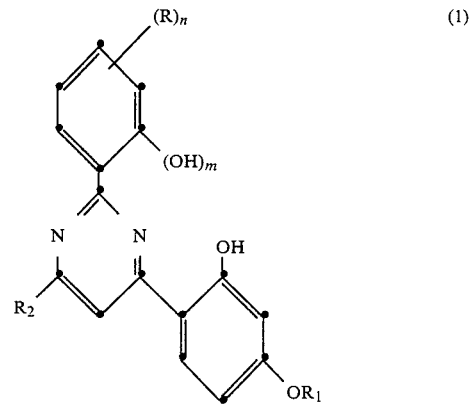

in which R is alkyl, alkoxy, halogen or hydroxyl, $R_1$ is alkyl, $R_2$ is hydrogen, halogen, alkyl, alkylamino, hydroxyalkylamino, aralkylamino, alkoxyalkylamino, alkenyl, alkoxy, alkoxy which is substituted by hydroxyl, carboxyl or $C_2$–$C_5$alkoxycarbonyl, alkenyloxy, phenyl or phenyl which is substituted by halogen, alkyl, hydroxy-$C_1$–$C_4$alkyl, alkenyloxy, alkoxy, hydroxyl or carboxy-$C_1$–$C_4$alkoxy, m is 0 or 1 and n is 0, 1 or 2, and also novel compounds of the formula (1) in which m and n are both 0 and $R_2$ is alkylamino, hydroxyalkylamino, aralkylamino or alkoxyalkylamino.

10 Claims, No Drawings

PROCESS FOR IMPROVING THE PHOTOCHEMICAL STABILITY OF DYEINGS ON POLYESTER FIBRE MATERIALS

This application is a continuation of application Ser. No. 156,771, filed Feb. 17, 1988.

The present invention relates to a process for improving the photochemical stability of dyeings on polyester fibre materials.

Dyed polyester fibre material is damaged if it is exposed to light and particularly if it is at the same time subjected to heat. Dyed materials of this type have therefore been protected against the effects of light and heat by means of UV absorbers of the benzophenone or benzotriazole type, but without achieving satisfactory results, because, when the dyeings are thermofixed and when they are exposed to light at elevated temperatures, these compounds have resulted in loss of products and hence insufficient protection, owing to their inadequate fastness to sublimation.

The stabilization of ligh-sensitive organic materials, for example wholly synthetic polymers and natural polymers, in particular pure addition polymers and pure condensation polymers, or condensation polymers crosslinked by addition polymerization, for example polyester resins, is known from GB-A No. 1,029,045. This relates, however, to the protection of these organic materials by incorporating the protecting agents in the organic polymeric mass, 2-o-hydroxyphenylpyrimidines being employed.

The object on which the present invention is based was to find a process for improving the photochemical stability of dyeings on polyester fibre materials which does not produce loss of product and which satisfies the present requirements.

This object is achieved by applying the protecting substances on the fibre materials instead of incorporating them in these materials.

The present invention therefore relates to a process for improving the photochemical stability of dyeings on polyester fibre materials by means of UV absorbers, which comprises treating the fibre material with a compound of the formula

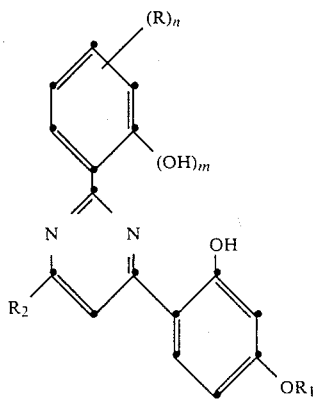

(1)

in which R is alkyl, alkoxy, halogen or hydroxyl, $R_1$ is alkyl, $R_2$ is hydrogen, halogen, alkyl, alkylamino, hyroxyalkylamino, aralkylamino, alkoxyalkylamino, alkenyl, alkoxy, alkoxy which is substituted by hydroxyl, carboxyl or $C_2$–$C_5$alkoxycarbonyl, alkenyloxy, phenyl or phenyl which is substituted by halogen, alkyl, hydroxy-$C_1$–$C_4$alkyl, alkenyloxy, alkoxy, hydroxyl or carboxy-$C_1$–$C_4$alkoxy, m is 0 or 1 and n is 0, 1 or 2.

As alkyl and alkoxy radicals, R and $R_2$ are radicals having 1 to 18 C atoms, such as methyl, ethyl, propyl, isopropyl, n-buryl, tertbutyl, pentyl, hexyl, octyl, decyl, dodecyl, tetradecyl, hexadecyl, octdecyl (stearyl), methoxy, ethoxy, propoxy, isopropoxy, n-butoxy, tertbutoxy, pentyloxy, hexyloxy, octyloxy, decyloxy, dodecyloxy and octadecyloxy. Alkyl radicals $R_1$ have 1 to 12, preferably 1 to 8, C atoms. They are radicals such as methyl, ethyl, propyl, isopropyl, n-butyl, tert-butyl, pentyl, hexyl, octyl, decyl and dodecyl.

Alkenyl radicals $R_2$ have 2 to 18 C atoms, such as vinyl, allyl, butenyl, isobutenyl, pentenyl, hexenyl, heptenyl, octenyl, decenyl, dodecenyl, tetradecenyl and octadecenyl.

Suitable alkenyloxy radicals $R_2$ are radicals having 2 to 18 C atoms, such as vinyloxy, allyloxy, butenyloxy, isobutenyloxy, pentenyloxy, hexenyloxy, heptenyloxy, octenyloxy, decenyloxy, dodecenyloxy, tetradecenyloxy and octadecenyloxy.

Alkylamino and hydroxyalkylamino radicals $R_2$ have 1 to 12, preferably 2 to 8, C atoms in the alkyl moiety. Examples of suitable radicals of this type are the methylamino, ethylamino, propylamino, isopropylamino, n-butylamino, tert-butylamino, pentylamino, hexylamino, octylamino, decylamino and dodecylamino radicals, and also the same radicals substituted by a hydroxyl group, preferably in a terminal position.

Alkoxyalkylamino radicals $R_2$ are radicals having a total of 2 to 8 C atoms, such as methoxymethylamino, methoxyethylamino, methoxypropylamino, methoxybutylamino, ethoxyethylamino, ethoxypropylamino, ethoxybutylamino, ethoxypentylamino, propoxyethylamino, propoxypropylamino, butoxyethylamino, butoxypropylamino and butoxybutylamino.

Aralkylamino radicals $R_2$ are preferably phenylalkyl radicals having 1 to 3 C atoms in the alkyl moiety, such as benzylamino, phenethylamino and phenylpropylamino.

As halogen substituents, R and $R_2$ can be bromine atoms and preferably chlorine atoms.

m and n are preferably 0.

Preferred compounds of the formula (1) are those in which $R_2$ is hydrogen, halogen, alkyl, alkenyl, alkoxy, alkoxy which is substituted by hydroxyl, carboxyl or $C_2$–$C_5$alkoxycarbonyl, alkenyloxy, phenyl or phenyl which is substituted by halogen, alkyl, hydroxy-$C_1$–$C_4$alkyl, alkenyloxy, alkoxy, hydroxyl or carboxy-$C_1$–$C_4$alkoxy.

Compounds which are of particular interest for the process according to the invention are those of the formula

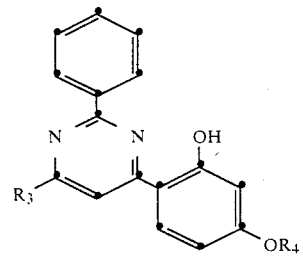

(2)

in which $R_3$ is hydrogen, chlorine, $C_1$–$C_4$alkyl, $C_1$–$C_8$alkylamino, hydroxy-$C_1$–$C_4$alkylamino, benzylamino, phenethylamino, $C_1$–$C_3$alkoxy$C_2$–$C_4$alkylamino, phenyl or phenyl which is substituted by $C_1$–$C_4$-alkyl, hydroxyl, alkoxy, alkenyloxy, hydroxy-$C_1$–$C_4$alkoxy or carboxy-$C_1$–$C_4$alkoxy, and $R_4$ is $C_1C_8$alkyl.

Preferred compounds of the formula (2) are those in which $R_3$ is hydrogen, chlorine, $C_1$–$C_4$alkyl, phenyl or phenyl which is substituted by $C_1C_4$alkyl, hydroxyl, alkoxy, alkenyloxy, hydroxy-$C_1C_4$alkoxy or carboxy-$C_1$–$C_4$alkoxy.

In the process according to the invention it is preferable to use compounds of the formula

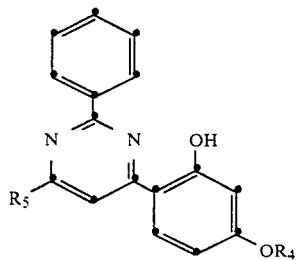

(3)

in which $R_4$ is as defined above and $R_5$ is $C_1$–$C_4$alkyl, chlorine, phenyl, o-hydroxyphenyl, $C_1$–$C_8$alkylamino, hydroxy-$C_1$–$C_4$alkylamino, phenethylamino or $C_1$–$C_3$alkoxy-$C_2C_3$alkylamino.

$R_5$ in the compounds of the formula (3) is preferably $C_1$–$C_4$alkyl, chlorine, phenyl or o-hydroxyphenyl.

The compounds of the formulae (1) to (3), which have also been disclosed as UV absorbers, are in part known and can be prepared in a manner known per se, for example by reacting, in the presence of Friedel-Crafts catalysts, halogenopyrimidines and compounds of the benzene series which contain a free or etherified hydroxyl group in an adjacent position to the resulting bond to the pyrimidine ring, and, if appropriate, other compounds of the benzene series (cf. British Patent Specification No. 1,029,145).

The novel compounds which can be used in accordance with the invention have the formula

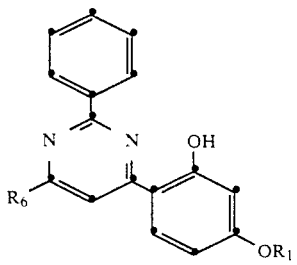

(4)

in which $R_1$ is as defined above and $R_6$ is alkylamino, hydroxyalkylamino, aralkylamino or alkoxyalkylamino. They can be prepared by reacting one mole of 4,6-dichloro-2-phenylpyrimidine with one mole of resorcinol in the presence of a Friedel-Crafts catalyst, and alkylating the resulting monochlorinated product by methods which are known per se.

The following are examples of suitable known compounds of the formulae (1), (2) and (3):

2,4-diphenyl-6-(2'-hydroxy-4'-methoxyphenyl)-pyrimidine, melting point 174°–175° C.;

2,4-diphenyl-6-(2'-hydroxy-4'-ethoxyphenyl)-pyrimidine, melting point 177°–178° C.;

2,4-diphenyl-6-(2'-hydroxy-4'-isopropoxyphenyl)-pyrimidine, melting point 123°–124° C.;

2,4-diphenyl-6-(2'-hydroxy-4'-butoxyphenyl)-pyrimidine, melting point 148°–149° C.;

2,4-diphenyl-6-(2'-hydroxy-4'-heptyloxyphenyl)-pyrimidine, melting point 103°–104° C.;

2-phenyl-4-chloro-6-(2'-hydroxy-4'-ethoxyphenyl)-pyrimidine, melting point 155°–156° C.;

2-phenyl-r-methyl-6-(2'-hydroxy-4'-ethoxyphenyl)-pyrimidine, melting point 125°–126° C.;

2-phenyl-4,6-di-(2'-hydroxy-4'-ethoxyphenyl)-pyrimidine, melting point 250° C.

Compounds of the formulae (1), (2) and (3) which are to be used as UV absorbers are employed in an amount of 0.05 to 7.5, preferably 0.20 to 3 and especially 0.5 to 2, % of the weight of the fibre material.

The following may be mentioned as examples of polyester fibre material which can be dyed in the presence of the UV absorbers mentioned: cellulose ester fibres, such as cellulose 2½-acetate fibres and triacetate fibres and, particularly, linear polyester fibres. Linear polyester fibres are to be understood here as meaning synthetic fibres which are obtained, for example, by subjecting terephthalic acid to condensation with ethylene glycol, or subjecting isophthalic acid or terephthalic acid to condensation with 1,4-bis-(hydroxymethyl)-cyclohexane, and also copolymers formed from terephthalic and isophthalic acids and ethylene glycol. The linear polyester hitherto employed almost exclusively in the textile industry consists of terephthalic acid and ethylene glycol.

The fibre materials can also be used as fabrics mixed with one another or with other fibres, for example mixtures of polyacrylonitrile/polyester, polyamide/polyester, polyester/cotton, polyester/viscose and polyester/wool.

The textile material to be dyed can be various types of material. Suitable materials are preferably piece goods, such as knitted or woven fabrics.

The disperse dyes to be used, which are only very slightly soluble in water and are present in the dye liquor for the most part in the form of a fine dispersion, can belong to a very wide variety of classes of dyes, for example to the acridone, azo, anthraquinone, coumarin, methine, perinone, naphthoquinone imine, quinophthalone, styryl or nitro dyes. Mixtures of disperse dyes can be employed in accordance with the invention.

Polyester/wool mixed fibre materials are preferably dyed in accordance with the invention using commercially available mixtures of anionic dyes and disperse dyes. Examples of the anionic dyes are the salts of monoazo, disazo or polyazo dyes, including formazan dyes, containing heavy metals or preferably free from metals, and of the anthraquinone, xanthene, nitro, triphenylmethane, naphthoquinone imine and phthalocyanine dyes. The anionic character of these dyes can be brought about solely by metal complex formation and/or, preferably, by acid, salt-forming substituents, such as carboxylic acid groups, sulfuric acid ester and phosphonic acid ester groups, phosphonic acid groups or sulfonic acid groups. The molecule of these dyes can also contain so-called reactive groupings which form a covalent bond with the wool.

The 1:1 or 1:2 metal complex dyes are of particular interest. The 1:1 metal complex dyes preferably contain one or two sulfonic acid groups. The metal present is a heavy metal atom, for example copper, nickel or especially chromium.

The 1:2 metal complex dyes contain, as the central atom, a heavy metal atom, for example a cobalt atom or especially a chromium atom. Two complex-forming components are attached to the central atom, at least one of which is a dye molecule, but preferably both are dye molecules. In this regard, the two dye molecules taking part in the formation of the complex can be identical with, or different from, one another. The 1:2 metal complex dyes can contain, for example, two azomethine molecules, a disazo dye and a monoazo dye or, preferably, two monoazo dye molecules. The azo dye molecules can contain groups imparting solubility in water, for example acid amide, alkylsulfonyl or the abovementioned acid groups. 1:2 cobalt or 1:2 chrmoium complexes of monoazo dyes containing acid amide or alkylsulfonyl groups or, in all, a single sulfonic acid group are preferred. It is also possible to employ mixtures of anionic dyes.

Fibre mixtures composed of polyester and cotton are dyed, as a rule, by means of a combination of disperse dyes and vat dyes, sulfur dyes, leuco vat ester dyes, direct dyes or reactive dyes, the polyester component being dyed with disperse dyes previously, at the same time or subsequently.

The vat dyes are fairly highly fused and heterocyclic benzoquinones or naphthoquinones, sulfur dyes and, in particular, anthraquinoid or indigoid dyes. Examples of vat dyes which can be used in accordance with the invention are listed in the Colour Index, 3rd Edition (1971), Volume 3, on pages 3649 to 3837 under the heading "Sulphur Dyes" and "Vat Dyes".

Examples of suitable direct dyes are the "Direct Dyes" mentioned on pages 2005 to 2478 of the Colour Index, 3rd Edition (1971), Volume 2.

The leuco vat ester dyes can be obtained, for example, from vat dyes of the indigo, anthraquinone or indanthrene series by reduction, for example by means of iron powder, and subsequent esterification, for example by means of chlorosulfonic acid, and are designated "Solubilised Vat Dyes" in the Colour Index, 3rd Edition (1971), Volume 3.

Reactive dyes are to be understood as meaning the customary dyes which form a chemical bond with the cellulose, for example the "Reactive Dyes" listed on pages 3391 to 3560 of the Colour Index, 3rd Edition (1971), Volume 3.

The amount of dyes to be added to the liquor depends on the depth of colour desired; in general, amounts of 0.01 to 10, preferably 0.02 to 5, % by weight, relative to the textile material employed, have proved suitable.

The compounds to be used in accordance with the invention can also be employed as a mixture with known carriers based on, for example, di-chlorobenzene, trichlorobenzene, methylbenzene, ethylbenzene, o-phenylphenol, benzylphenol, diphenyl ether, chlorobiphenyl, methylbiphenyl, cyclohexanone, acetophenone, alkylphenoxyethanols, mono-, di- or tri-chlorophenoxyethanol, mono-, di- or tri-chlorophenoxypropanol, pentachlorophenoxyethanol, alkyl phenylbenzoates or, in particularly, based on biphenyl, methyl biphenyl ether, dibenzyl ether, methyl benzoate, butyl benzoate and phenyl benzoate.

Carriers are preferably employed in an amount of 0.5 to 2 g/l of liquor or 5 to 10% by weight, relative to the compounds to be used.

Depending on the textile material to be treated, the dyebaths can contain, in addition to the dyes and the compounds to be employed in accordance with the invention, wool protection agents, oligomer inhibitors, oxidizing agents, anti-foams, emulsifiers, levelling assistants, retarders and, preferably, dispersing agents.

The dispersing agents are used, in particular, to achieve good dispersion of the disperse dyes. Dispersing agents which are generally customary are suitable when dyeing with disperse dyestuffs.

Suitable dispersing agents are preferably sulfated or phosphated adducts of 15 to 100 moles of ethylene oxide, or preferably propylene oxide, onto polyhydric aliphatic alcohols having 2 to 6 carbon atoms, for example ethylene glycol, glycerol or pentaerythritol, or onto amines which have 2 to 9 carbon atoms and at least 2 amino groups or an amino group and a hydroxyl group and also onto alkylsulfonates having 10 to 20 carbon atoms in the alkyl chain, alkylbenzenesulfonates having a linear or branched alkyl chain with 8 to 20 c arbon atoms in the alkyl chain, for example nonylbenzenesulfonate, dodecylbenzenesulfonate, 1,3,5,7-tetramethyloctylbenzenesulfonate or octadecylbenzenesulfonate, and also alkylnaphthalenesulfonates or sulfosuccinic acid esters, such as sodium dioctylsulfosuccinate.

Anionic dispersing agents which have proved particularly advantageous are ligninsulfonates, polyphosphates and, preferably, formaldehyde condensation products formed from aromatic sulfonic acids, formaldehyde and, if appropriate, monofunctional or bifunctional phenols, for example from cresol, β-naphtholsulfonic acid and formaldehyde, from benzenesulfonic acid, formaldehyde and naphthalenic acid, from naphthalenesulfonic acid and formaldehyde or from naphthalenesulfonic acid, dihydroxydiphenyl sulfone and formaldehyde. The disodium salt of di-(6-sulfonaphth-2-yl)-methane is preferred.

It is also possible to employ mixtures of anionic dispersing agents. The anionic dispersing agents are normally in the form of their alkali metal salts, ammonium salts or amine salts. These dispersing agents are preferably used in an amount of 0.1 to 5 g/l of liquor.

Depending on the dye and substrate to be used, the dyebaths can also contain, in addition to the assistants already mentioned, customary additives, advantageously electrolytes, such as salts, for example sodium sulfate, ammonium sulfate, sodium phosphates or polyphosphates, ammonium phosphates or polyphosphates, metal chlorides or metal nitrates, such as sodium chloride, calcium chloride, magnesium chloride or calcium nitrates, ammonium acetate or sodium acetate and/or acids, for example mineral acids, such as sulfuric acid or phosphoric acid, or organic acids, advantageously lower aliphatic carboxylic acids, such as formic, acetic or oxalic acid, and also alkalis or alkali donors or complex-formers. The acids are used, in particular, to adjust the pH of the liquors used in accordance with the invention, which as a rule is 4 to 6.5, preferably 4.5 to 6.

The dyeings are advantageously carried out from an aqueous liquor by the exhaustion process. The liquor ratio can, accordingly, be selected within a wide range, for example 1:4 to 1:100, preferably 1:6 to 1:50. The temperature at which dyeing is carried out is at least 50° C. and, as a rule, is not higher than 140° C. It is preferably within the range from 80° to 135° C.

Linear polyester fibres and cellulose triacetate fibres are preferably dyed by the so-called high-temperature process in closed machines which are advantageously also pressure-resistant, at temperatures above 100° C., preferably between 110° and 135° C., and under pressure. Examples of suitable closed vessels are circulation machines, such as cheese or beam dyeing machines, winches, jet-dyeing or drum dyeing machines, muff dyeing machines, paddles or jigs.

Cellulose 2½-acetate fibres are preferably dyed at temperatures of 80°–85° C.

The dyeing process according to the invention can be carried out either by first treating the materials to be dyed briefly with the compounds and then dyeing it or, preferably, by treating it with the compounds and the dye simultaneously.

It is preferable to work the material to be dyed for 5 minutes at 50° to 80° C. in the bath which contains the dye, the compound and, if appropriate, further additives, the pH of which has been adjusted to a value from 4.5 to 5.5, to raise the temperature to 100° to 110° C. in the course of 10 to 20 minutes and to 125° to 130° C. in the course of a further 10 to 20 minutes and to keep the dye liquor at this temperature for 15 to 90 minutes, preferably 30 minutes.

The dyeings are finished by cooling the dye liquor to 50° to 80° C., rinsing the dyeings with water and, if necessary, by cleaning them in a customary manner in an alkaline medium under reductive conditions. The dyeings are then rinsed again and dried. In the event that carriers are used, it is advantageous, in order to improve the fastness to light, to subject the dyeings to a heat treatment, for example thermosol treatment, which is preferably carried out at 160° to 180° C. for 30 to 90 seconds. If vat dyes are used for the cellulose component, the goods are first treated in a customary manner with hydrosulfite at a pH of 6 to 12.5 and then with oxidizing agent, and finally are washed.

The process according to the invention stabilizes polyester fibre materials photochemically, i.e. protected against exposure, especially exposure under hot conditions, to visible and UV light.

A particularly outstanding advantage of the process according to the invention is that, compared with processes hitherto known for the photochemical stabilization of polyester fibre materials, no pretreatment or after-treatment of the fibre materials is necessary.

In the following instructions for preparation and examples, the percentages are by weight unless otherwise specified. In the case of the dyes and the UV absorbers, the quantities relate to formulations. Any five-figure Colour Index numbers (C.I.) relate to the 3rd edition of the Colour Index.

INSTRUCTIONS FOR PREPARATION A

Preparation of a compound of the formula (1)

22.5 g of 4,6-dichloro-2-phenylpyrimidine and 11.0 g of resorcinol are dissolved in 150 ml of nitrobenzene, and 13.3 g of anhydrous aluminium chloride are added. The mixture is then heated to 75°–80° C. and is stirred at this temperature for 12 hours. When the reaction mixture has cooled to room temperature and has been decomposed with hydrochloric acid and water, the nitrobenzene is removed by steam distillation. This gives 2-phenyl-4-chloro-6-(2',4'-dihydroxyphenyl)pyrimidine in a good yield, melting point 213°–214° C. The product is then alkylated in a manner known per se, for example by means of diethyl sulfate in accordance with Example 9 of GB-A 1,029,045. This gives 2-phenyl-4-chloro-6-(2'-hydroxy-4'-ethoxyphenyl)-pyrimidine of melting point 155°–156° C.

22.9 g of 2-phenyl-4-chloro-6-(2'-hydroxy-4'-ethoxyphenyl)-pyrimidine, 12.8 g of ethanolamine and 120 ml of cyclohexanol are heated at 140°–145° C. for 3 hours. After cooling to 100° C., 120 ml of water are run into the reaction mixture. The mixture is then stirred for 10 minutes. The product separates into layers when the stirrer has been switched off. The aqueous layer is separated off from the cyclohexanol layer, and the latter is evaporated to dryness. The residual product is recrystallized from ethanol to give 22 g of the nearly colourless product of the formula

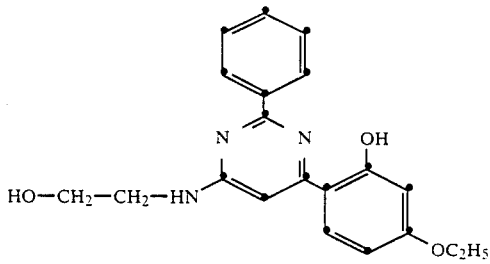

melting point 162°–164° C.

The following compounds are obtained similarly: 2-phenyl-4-(3'hydroxypropylamino)-6-(2''-hydroxy-4''-ethoxyphenyl)-pyrimidine, melting point 129°–131° C., 2-phenyl-4-(4'-hydroxybutylamino)-6-(2''-hydroxy-4''-ethoxyphenyl)-pyrimidine, melting point 94°–95° C.; 2-phenyl-4-ethylamino-6-(2'-hydroxy-4'-ethoxyphenyl)-pyrimidine, melting point 107°–108° C.; 2-phenyl-4-octylamino-6-(2'-hydroxy-4'-ethoxyphenyl)pyrimidine, oil; 2-phenyl-4-methoxypropylamino-6-(2'-hydroxy-4'-ethoxyphenyl)-pyrimidine, oil and 2-phenyl-4-phenethylamino-6-(2'-hydroxy-4'-ethoxy-phenyl)-pyrimidine, melting point 117°–118° C.

INSTRUCTIONS FOR PREPARATION B

Preparation of a UV absorber dispersion 20 g of quartz microspheres (diameter approx. 1 mm) and 5 g of a condensation product formed from naphthalenesulfonic acid and formaldehyde, as a dispersing agent, dissolved in 7.5 ml of water, are added to 5 g of a UV absorber, and the mixture is ground by means of a stirrer operating at approx. 1600 revolutions per minute until the particle size is below 2 μm. The dispersion is then separated off from the quartz microspheres by means of a fine mesh sieve, and is standardized with water to a 20% content of active substance. 0.3% of carboxymethylcellulose is then stirred in in order to stabilize the dispersion.

EXAMPLE 1

13 series of pieces of Diolen ® knitted fabric, in each case comprising 3 pieces each weighing 10 g, are treated in an HT dyeing machine with liquors which contain 2 g of ammonium sulfate, 0.5 g of a dispersion stabilizer, 0.25 g of a dispersing agent, 0.2% of C.I. Disperse Orange 53 (as an approx. 35% dispersion) and in each case 1.65 or 5.0% of the UV absorbers (in every case as 20% dispersions):

I     2-(2'-hydroxy-3'-tert-butyl-5'-methylphenyl)-5-chlorobenzotriazole;

II 2,2'-dihydroxy-4,4'-dimethoxybenzophenone;

III     2-phenyl-4-methyl-6-(2'-hydroxy-4'-ethoxyphenyl)-pyrimidine;

IV     2,4-diphenyl-6-(2'-hydroxy-4'-ethoxyphenyl)-pyrimidine;

V     2-phenyl-4-chloro-6-(2'-hydroxy-4'-ethoxyphenyl)-pyrimidine or

VI 2-phenyl-4,6-di-(2'-hydroxy-4'-ethoxyphenyl)-pyrimidine per liter, and which have been adjusted to pH 5 with formic acid. A dyeing without added UV absorber is also prepared.

Dyeing is carried out in bombs at a liquor ratio of 1:10 by first treating the pieces of knitted fabric at 50° C. for 5 minutes, and then raising the temperature, first to 100° C. in 10 minutes and then to 130° C. in a further 10 minutes. Dyeing is carried out at this temperature for 30 minutes and the goods are then cooled to 50° C., rinsed with warm water, centrifuged and dried in a circulating air oven at 80° C. The 13 series comprising in each case 3 pieces weighing 10 g each are then subdivided into 3 series. Whereas series 1 remains untreated, series 2 and series 3 are treated in a hot air thermofixing apparatus (for example the apparatus made by W. Mathis, Niederhasli, Switzerland), series 2 for 60 seconds at 180° C. and series 3 for 60 seconds at 200° C.

The fastness to light under hot conditions of all the 39 samples is then checked by the Ford EU BO 50-2 method (testing instructions FLT EU BO 50-2; test apparatus Xenotest 1200, even-speed; duration of test 48 hours; black body temperature 75° C.; humidity 80%). The following results are obtained:

TABLE I

| UV absorber | Amount % | FORD light-fastness values | | |
|---|---|---|---|---|
| | | — | 180° C./60 seconds | 200° C./60 seconds |
| none | — | 1–2 | 1–2 | 1–2 |
| I | 1.65 | 3–4 | 3–4 | 2–3 |
| | 5.0 | –4 | 3–4 | 3 |
| II | 1.65 | 3–4 | 3–4 | 3 |
| | 5.0 | 4 | 3–4 | 3+ |
| III | 1.65 | 3–4 | 3–4 | 3–4 |
| | 5.0 | 4 | 4 | 4 |
| IV | 1.65 | 3–4 | 3–4 | 3–4 |
| | 5.0 | 4 | 4 | 4 |
| V | 1.65 | 3–4 H | –4 | 4 |
| | 5.0 | –4 | 4 | –4–5 |
| VI | 1.65 | 3 H | 3 H+ | 3–4 H |
| | 5.0 | 4 | 4 | 4+ |

The assessment of fastness to light shows clearly that, in the case of the known UV absorbers I and II, a marked reduction in the values takes place at 200° C., whereas, in the case of the UV absorbers which can be used in accordance with the invention, the values remain constant.

EXAMPLE 2

The procedure is as described in Example 1, with the exception that no dye is employed. Thermofixing is carried out under the same conditions. The amounts of UV absorber present on the fibre are determined by diffuse reflection measurements on the pieces of knitted fabric; the K/S values are quoted as a characteristic concentration value.

TABLE II

| UV absorber | Amount % | *K/S VALUES (in %) | | |
|---|---|---|---|---|
| | | — | 180° C./60 seconds | 200° C./60 seconds |
| I | 1.65 | 25.1 (100%) | 19.0 (75%) | 11.3 (45%) |
| | 5.0 | 57.1 (100%) | 43.2 (75.7%) | 28.7 (50.3%) |
| II | 1.65 | 26.1 (100%) | 21.5 (82.4%) | 18.0 (68.9%) |
| | 5.0 | 46.6 (100%) | 31.9 (68.5%) | 25.0 (53.6%) |
| III | 1.65 | 23.7 (100%) | 22.2 (93.7%) | 17.8 (75.1%) |
| | 5.0 | 49.0 (100%) | 36.5 (74.5%) | 29.9 (61.0%) |
| IV | 1.65 | 22.3 (100%) | 21.2 (95.5%) | 16.2 (72.6%) |
| | 5.0 | 48.5 (100%) | 42.7 (88.0%) | 43.9 (90.5%) |
| V | 1.65 | 29.1 (100%) | 29.2 (100%) | 27.2 (93.5%) |
| | 5.0 | 37.1 (100%) | 41.2 (>100%) | 50.5 (>100%) |
| VI | 1.65 | 25.1 (100%) | 22.6 (90%) | 21.8 (87.0%) |
| | 5.0 | 62.6 (100%) | 67.4 (>100%) | 68.4 (>100%) |

*measured at 340 nm

The K/S values show clearly that the loss of UV absorber during thermofixing is greater for products I and II than for product III and IV. In the higher concentrations, products V and VI show a tendency to redevelopment.

EXAMPLE 3

Grey-brown dyeings with and without UV absorber are produced on 7 10 g hanks of a Terylene ® staple yarn, dyeing being carried out as described in Example 1, using the following mixture of dyes:
 1.00% of C.I. Disperse Yellow 42
 0.30% of C.I. Disperse Blue 60
 0.15% of C.I. Disperse Violet 57
 0.40% of C.I. Disperse Red 302

The compounds I, III and V are used as UV absorbers in amounts of 1.5% and 4.5% (in every case as 20% dispersions). The fastness to light under hot conditions of the dyeings is then determined by the Ford EU BO 50-2 method (exposure 48 hours and 96 hours) and by the method of DIN 75,202, draft (Fakra exposure: 96 hours and 192 hours). The following results are obtained:

TABLE III

| UV absorber | Amount % | LIGHT-FASTNESS VALUES UNDER HOT CONDITIONS AS MEASURED IN | | | |
|---|---|---|---|---|---|
| | | Fakra 96 hours | Fakra 192 hours | Ford 48 hours | Ford 96 hours |
| none | — | 3–4 | 3 | 3–4 | 3 |
| I | 1.5 | 3–4 | 3–4 | 3–4 | 3 |
| | 4.5 | 4–5 | 4 | +4 | 3–4 |
| III | 1.5 | 4 | 4 | 4 | 3–4+ |
| | 4.5 | –4–5 | –4 | 4+ | 4 |
| V | 1.5 | 4 | 3–4+ | 3–4H+ | –3–4 H |
| | 4.5 | –4–5 | –4 | 4 | –4 |

What we claim is:
1. A process for improving the photochemical stability of dyeings on polyester fibers which process comprises applying on said fibers from an aqueous liquor by the exhaustion process a compound of the formula

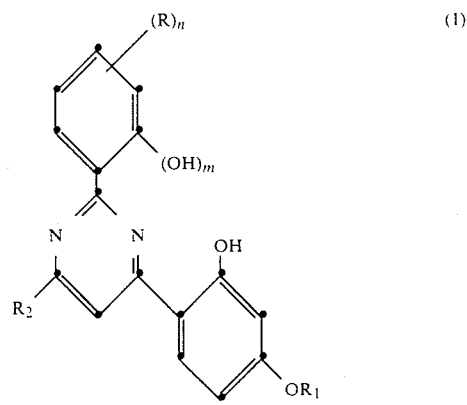

in which R is alkyl, alkoxy, halogen or hydroxyl, $R_1$ is alkyl, $R_2$ is hydrogen, halogen, alkyl, alkylamino, hydroxyalkylamino, aralkylamino, alkoxyalkylamino, alkenyl, alkoxy, alkoxy which is substituted by hydroxyl, carboxyl or $C_2$-$C_5$alkoxycarbonyl, aklenyloxy, phenyl or phenyl which is substituted by halogen, alkyl, hydroxy-$C_1$-$C_4$alkyl, alkenyloxy, alkoxy, hydroxyl or carboxy-$C_1$-$C_4$alkoxy, m is 0 to 1 and n is 0, 1 or 2.

2. A process according to claim 1, wherein a compound of the formula

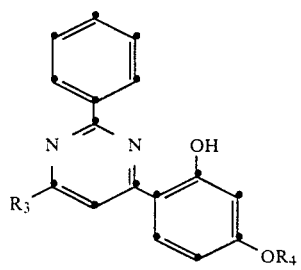

(2)

in which $R_3$ is hydrogen, chlorine, $C_1$-$C_4$alkyl, $C_1$-$C_8$alkylamino, hydroxy-$C_1$-$C_4$alkylamino, benzylamino, phenethylamino, $C_1C_3$alkoxy-$C_2$-$C_4$alkylamino, phenyl or phenyl which is substituted by $C_1$-$C_4$alkyl, hydroxyl, alkoxy, alkenyloxy, hydroxy-$C_1$-$C_4$alkoxy or carboxy-$C_1$-$C_4$alkoxy, and $R_4$ is $C_1$-$C_8$alkyl, is used.

3. A process according to claim 1, wherein a compound of the formula

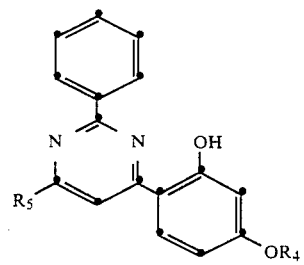

(3)

in which $R_4$ is $C_1$-$C_8$alkyl and $R_5$ is $C_1$-$C_4$alkyl, chlorine, phenyl, o-hydroxyphenyl, $C_1$-$C_8$alkylamino, hydroxy-$C_1$-$C_4$alkylamino, phenethylamino or $C_1$-$C_3$alkoxy-$C_2$-$C_3$alkylamino, is used.

4. A process according to claim 1, wherein $R_2$ is hydrogen, halogen, alkyl, alkenyl, alkoxy, alkoxy which is substituted by hydroxyl, carboxyl or $C_2$-$C_5$alkoxycarbonyl, alkenyloxy, phenyl or phenyl which is substituted by halogen, alkyl, hydroxy-$C_1$-$C_4$alkyl, alkenyloxy, alkoxy, hydroxyl or carboxy-$C_1$-$C_4$alkoxy.

5. A process according to claim 2, wherein $R_3$ is hydrogen, chlorine, $C_1$-$C_4$alkyl, phenyl or phenyl which is substituted by $C_1$-$C_4$alkyl, hydroxyl, alkoxy, alkenyloxy, hydroxy-$C_1$-$C_4$alkoxy or carboxy-$C_1$-$C_4$alkoxy.

6. A process according to claim 3, wherein $R_5$ is $C_1$-$C_4$alkyl, chlorine, phenyl or o-hydroxyphenyl.

7. A process according to claim 1, wherein the compound of the formula (1) to be employed is used in an amount of 0.5 to 7.5% by weight of the fibers.

8. A process according to claim 1, wherein the compound of the formula (1) is added directly to the dyebath.

9. The polyester fibers which has been treated by the process according to claim 1.

10. A compound of the formula

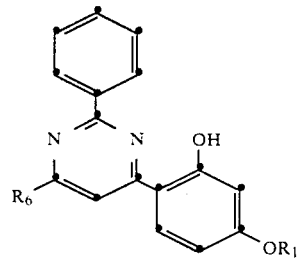

(4)

in which $R_1$ is alkyl and $R_6$ is alkylamino, hydroxyalkylamino, aralkylamino or alkoxyalkylamino.

* * * * *